(12) United States Patent
Meister et al.

(10) Patent No.: US 7,870,616 B2
(45) Date of Patent: Jan. 11, 2011

(54) PROBE ARRANGEMENT

(75) Inventors: André Meister, La Sagne (CH); Jérôme Polesel-Maris, Neuchâtel (CH); Michael Gabi, Zürich (CH); Tomaso Zambelli, Zürich (CH); Janos Vörös, Zürich (CH)

(73) Assignee: CSEM Centre Suisse D'Electronique Et de Microtechnique SA, Neuchatel (CH)

( * ) Notice: Subject to any disclaimer, the term of this patent is extended or adjusted under 35 U.S.C. 154(b) by 321 days.

(21) Appl. No.: 12/117,801

(22) Filed: May 9, 2008

(65) Prior Publication Data

US 2008/0302960 A1     Dec. 11, 2008

Related U.S. Application Data

(60) Provisional application No. 60/928,904, filed on May 11, 2007.

(51) Int. Cl.
*H01J 37/252* (2006.01)
(52) U.S. Cl. .................................. 850/21; 73/105
(58) Field of Classification Search .............. 850/14, 850/21; 73/105
See application file for complete search history.

(56) References Cited

U.S. PATENT DOCUMENTS

| | | | |
|---|---|---|---|
| 5,750,989 A | * | 5/1998 | Lindsay et al. ............. 850/14 |
| 6,353,219 B1 | | 3/2002 | Kley |
| 7,045,780 B2 | | 5/2006 | Kley |
| 7,690,325 B2 | * | 4/2010 | Henderson et al. .......... 118/300 |

FOREIGN PATENT DOCUMENTS

JP     200434277     5/2004

OTHER PUBLICATIONS

Ratneshwar Lal et al., Imaging Molecular Structure and Physiological Function of Gap Junctions and Hemijunctions by Multimodal Atomic Force Microcopy, Microscopy Research and Technique, 2001, pp. 273-288, vol. 52, XP-002489960.

Roger Proksch et al., Imaging the Internal and External Pore Structure of Membranes in Fluid: TappingMode Scanning Ion Conductance Microscopy, Biophysical Journal, Oct. 1996, pp. 2155-2157, vol. 71, XP-000961352.

(Continued)

*Primary Examiner*—Kiet T Nguyen
(74) *Attorney, Agent, or Firm*—Martin Fleit; Paul D. Bianco; Fleit Gibbons Gutman Bongini & Bianco PL

(57) ABSTRACT

A probe arrangement with a probe for local electrophysiological analysis of cells (4) such as patch-clamp techniques for use with atomic force microscopy, has a probe with a cantilever arm (2) connected to a probe holder (3). The probe has a probe tip (4) at a probing end (5) of the cantilever arm (2) and a fluid channel (6) in the cantilever arm (2) connecting a probe tip aperture (7) with a fluid reservoir (8) via a duct (9). The fluid channel (6), the duct (9) and the fluid reservoir (8) are adapted to be filled with a fluid solution (10) enabling ion transport for electrophysiological analysis. A first electrode (15) for electrophysiological analysis is placed in the fluid reservoir (8) and/or in the duct (9) and/or in the fluid channel (6).

14 Claims, 4 Drawing Sheets

OTHER PUBLICATIONS

Keun-Ho Kim et al., A Novel AFM Chip for Fountain Pen Nanolithography—Design and Microfabrication, Mat. Res. Soc. Symp. Proc., 2004, pp. A5.56.1-A5.56.6, vol. 782, XP-002351776.

Andreas Bruckbauer et al., Writing with DNA and Protein Using a Nanopipet for Controlled Delivery, J. Am. Chem. Soc., 2002, pp. 8810-8811, vol. 124, XP-002489961.

European Search Report dated Aug. 11, 2008 for EP08155990 (related application).

Erwin Neher et al , The Extracellular Patch Clamp: A Method for Resolving Currents through Individual Open Channels in Biological Membranes, (1978) 375, pp. 219-228, European Journal of Physiology.

Andreas Bruckbauer et al., Writing with DNA and Protein Using a Nanopipet for Controlled Delivery, pp. 8810-8811, vol. 124 , American Journal of Chem. Soc. (2002).

Xing Chen et al., A cell nanoinjector based on carbon nanotubes, (May 15, 2007) p. 8218-8222, vol. 104 No. 20, PNAS.

P. K. Hansma et al., The scanning ion-Conductance Microscope. (Feb. 3, 1989) Science, p. 641-643, vol. 243 No. 4891.

Aaron Lewis et al., Fountain pen nanochemistry: Atomic force control of chrome etching. (Oct. 25, 1999) p. 2689-2691, vol. 75 No. 17, Applied Phs. Letters, Am. Inst of Physics.

* cited by examiner

PROBE ARRANGEMENT

This patent application claims priority from U.S. provisional patent application 60/928,904, filed on May 11, 2007, the application which is incorporated herein by reference in its entirety.

FIELD OF THE INVENTION

The invention relates to a probe arrangement with a probe for electrophysiological analysis of material (e.g. biological material) for use with atomic force microscopy (AFM) according to the preamble of claim 1 and a method for the automatic approach and scanning of one or more samples of, e.g., biological material, with such a probe arrangement according to the preamble of claim 11.

SUMMARY OF SOME EMBODIMENTS OF THE INVENTION

The present invention concerns a cantilevered probe arrangement comprising a plurality of tips, wherein the force between the tips and a micro-sized sample of material such as, for example, a biological material, may be controlled by measuring the deflection of the cantilevered probe. The probe arrangement includes microchannels that may be controllable by a drive for performing analysis and/or manipulation of micro-sized samples of material, in, e.g., a fluid environment constituting, for example, biological material. The cantilever probe tip may for example be employed to perform electrophysiological tests in accordance to, for example, various modes such as a static and a scanning mode of samples of biological material such as biological tissue; an individual cell as well as elements thereof including vesicles, cell membrane and portions thereof, lipid bilayers and artificial lipid bilayers. The microchannels enable the release of fluids and the collection of samples in the very range where the electrophysiological tests are performed. In embodiments of the invention, the drive is operatively coupled with a force-feedback module enabling the control of stress applied on the sample(s). Hence, a user of the cantilever probe may define whether a gentle contact or a deep indentation is to be caused by the probe.

One of the main applications of embodiments of the present invention is associated to cell biology, such as intracellular injection or sampling of the cytoplasm, extracellular drug release or sampling of the environmental buffer in relative proximity close to the cell by means of the force-controlled cantilever probe tip. But the invention is not restricted to the aforementioned applications. Other applications may also be considered and may include, for example, local spotting of material, local electrochemistry and force controlled patch-clamping.

In embodiments of the invention, a probe arrangement with a probe for analysis of material for use with atomic force microscopy (AFM) may include: a cantilever arm connected to a probe holder.

In embodiments of the invention, the probe arrangement may include a probe tip at a probing end of the cantilever arm.

In embodiments of the invention, the probe arrangement may include a fluid channel in the cantilever arm connecting a probe tip aperture with a fluid reservoir via a duct wherein the fluid channel, the duct and the fluid reservoir are adapted to be filled with a fluid solution enabling ion transport for electrophysiological analysis, wherein a first electrode is suspended in at least one of the following locations: the fluid reservoir in the duct; and in the fluid channel.

In embodiments of the invention, the probe arrangement is microfabricated and connected to an AFM head via the probe holder.

In embodiments of the invention, the probe holder may be made of a polymer block.

In embodiments of the invention, the cantilever arm of the probe arrangement may include at least one of the probe tips. The probe arrangement may include a plurality of fluid reservoirs, each being connected via a separate duct to the respective fluid channels of the cantilever arm.

In embodiments of the invention, at least one of the fluid reservoirs is equipped with a means for pressure and flow control, enabling the probe arrangement to selectably ejecting and sucking fluid via the fluid channel.

In embodiments of the invention, the probe tip may be tapered and may have a flattened tip, and a probe tip aperture that is centered and aligned with the rotational axis of the tapered shape.

In embodiments of the invention, the probe tip is tapered and terminates in a sharp tip and a probe tip aperture may be arranged off-axis at the side of the tapered surface.

In embodiments of the invention, the probe tip is tapered and a probe tip aperture is arranged slightly off-axis on a flattened plateau surface slightly below the sharp tip.

In embodiments of the invention, the probe arrangement is adapted to operate in a fluid environment of a fluid chamber comprising a buffer fluid wherein a second electrode is placed in the buffer fluid.

In embodiments of the invention, a method for the automatic approach and scanning of cell surfaces and the acquisition of real time topographical images of the cell and features of its membrane by using a force feedback control system for controlling the probe arrangement may include the following steps: obtaining a force-feedback whilst performing at least one of the following in accordance to the obtained force-feedback: selectably bringing the probe into contact with either one of the following: the cell, the cell membrane, and into the vicinity of the cell membrane; and selectably performing through at least one fluid channel of the probe either one of the following: releasing and withdrawing a fluid; and performing local electrophysiological measurements.

In embodiments of the invention, the method may include, for example, traversing with the probe tip the cell membrane to the interior of the cell.

In embodiments of the invention, the method may include, for example, the selectably releasing and withdrawing a fluid to or from the interior of the cell.

In embodiments of the invention, the method may include, for example, selectably performing either one electrophysiological measurements before and during and after bringing the probe into contact with either one of the cell membrane the vicinity of the cell membrane.

In embodiments of the invention, the method may include, for example, selectably applying electrical stimulation.

In embodiments of the invention, the method may include, for example, selectably employing an electrochemical current and voltage signal probed by the first electrode.

In embodiments of the invention, the method may include, for example, using the probe in contact on the sample for patch-clamp techniques.

BACKGROUND OF THE INVENTION

Nanoscale Dispensing (NADIS)

In NADIS, a chip that includes a microchannel is employed to deposit small amounts of fluids or droplets on a substrate. The fluid is dispensed manually into a reservoir located in the probe chip, without any external pressure applied to the fluid; only capillary pressure is used to fill the hollow cantilever and to dispense the fluid from the cantilever into the reservoir. However, the probe chip is not coupled with a fluid connection through a special designed probe holder, but is placed on a standard probe holder of a standard AFM instrument.

Patch Clamp Technique:

The Patch clamp technique, described by E. Neher, B. Sakmann and J. H. Steinbach in Pflugers Archiv-European Journal of Physiology 1978, 375, 219 and which is incorporated in herein in its entirety, is used in electrophysiological analysis to study individual ion channels in cell membranes. The patch clamp technique is used to study excitable cells such as neurons, muscle or beta cells of the pancreas. In classical patch clamp technique, the electrode being employed is a hollow glass pipette or a flat surface punctured with tiny holes in so called "planar patch clamp technique". Both the pipette as well as the tiny holes of the flat surface are filled with a high molar salt solution as a conducting electrode allowing a researcher to keep the voltage constant while observing changes in current. Alternatively, the cell can be "current clamped", i.e., the current is kept at substantially constant value while changes in membrane potential are observed. The patch clamp technique may only be implemented by highly trained technicians because the pipette is moved by micromanipulators and the position is manually controlled by optical microscopy. The height (z-position) of the pipette is controlled manually only by the focus of the very pipette tip. Consequently, cells are often ruptured, possibly causing the ruptured cells to become not analyzable. This may result in a frustrating, inefficient and time-consuming probing experience, in particular if more than one cell of a network is to be patched.

Microinjection and Patch Clamping Tools

P. K. Hansma et al., disclose in Science 243 (1989) 641, which is incorporated by reference in its entirety, a technique named scanning ion conductance microscopy (SICM). The probe of a microscope employing SICM is an electrolyte-filled micropipette. As the tip of the micropipette approaches a sample, the ion conductance and therefore the current decrease since the gap through which ions can flow, is reduced in size. A feedback mechanism can be used to maintain a predetermined conductance and to determine in turn the distance of the micropipette to the surface of the probe to be sampled. This technique can be employed to spot biotin-modified DNA onto streptavidin-coated and positively charged glass surfaces (cf. to A. Bruckbauer et al. JACS 124 (2002) 8810, which is incorporated herein by reference in its entirety).

Chen et al. disclose in PNAS 104 (2007) 8218, which is incorporated herein in its entirety, a nanoinjector (hereinafter referred to as "nanoneedle") that employs nanotubes to deliver cargo into cells. A single multiwalled carbon nanotube attached to an AFM tip is adapted to deliver cargo by means of a disulfide-based linker. Depth of penetration of the nanoneedle into cell membranes is controlled by the AFM, whereby the penetration causes a reductive cleavage of the disulfide bonds within the cell's interior, which in turn results in the release of the cargo inside the cells, after the nanoneedle's AFM-controlled retraction from the inside of the cell. The nanoneedle's capabilities were demonstrated by injection of protein-coated quantum dots into live human cells.

Nano Fountain Pen:

Lewis et al. disclose in "Fountain pen nanochemistry: Atomic force control of chrome etching" published in Applied Physics Letters Volume 75, Number 17, 25 October 1999, which is incorporated herein by reference in its entirety, a general method for affecting chemical reactions with a high degree of spatial control that has potentially wide applicability in science and technology. The described technique is based on complexing the delivery of fluids (i.e., liquid or gaseous materials) through a cantilevered micropipette with an atomic force microscope that is totally integrated into a conventional optical microscope. Controlled etching of chrome is demonstrated without detectable effects on the underlying glass substrate. This simple combination allows for the nanometric spatial control of the whole world of chemical reactions in defined regions of surfaces. Applications of the technique in critical areas such as mask repair are likely.

Tapered Microcapillaries:

Several groups developed dispensing techniques using tapered microcapillaries. The motion with respect to the surface of such probes is controlled optically or by a shear-force feedback control using a dither PZT piezo. But all these techniques suffer from the absence of a real force sensor that measures the normal force exerted on the sample. Furthermore, all this probes have only circular apertures located at the very end of the tapered microcapillaries U.S. Pat. No. 6,353,219, which is incorporated herein by reference in its entirety, discloses an object inspection and/or modification system and method. It is concerned with a SPM (scanning probe microscopy) system for modifying an object that includes producing measurements indicative of modifications to be made to the object. The object may be a biological cell or material. In accordance with the measurements, one or more SPM probes are manipulated to effect the modifications. The device includes a fluid material delivery tool having a cantilever with a tapered tip and a capillary in the core material of the tip. The capillary is connected to a duct in the cantilever arm and the duct is connected to a pumping chamber.

U.S. Pat. No. 7,045,780, which is incorporated herein by reference in its entirety, discloses a scanning probe microscopy inspection and modification system. It is concerned with a microstructured SPM (scanning probe micicroscopy) probe for use in inspecting an object by making SPM measurements of the object, such as AFM (atomic force microscopy), STM (scanning tunnelling microscopy) and other techniques. The probe has several cantilevers, each connected to a tip activation control circuit.

BRIEF DESCRIPTION OF THE DRAWINGS

Features of the invention will become more clearly understood in light of the ensuing description of some embodiments thereof, given by way of example only, with reference to the accompanying figures, wherein.

Figure 1:
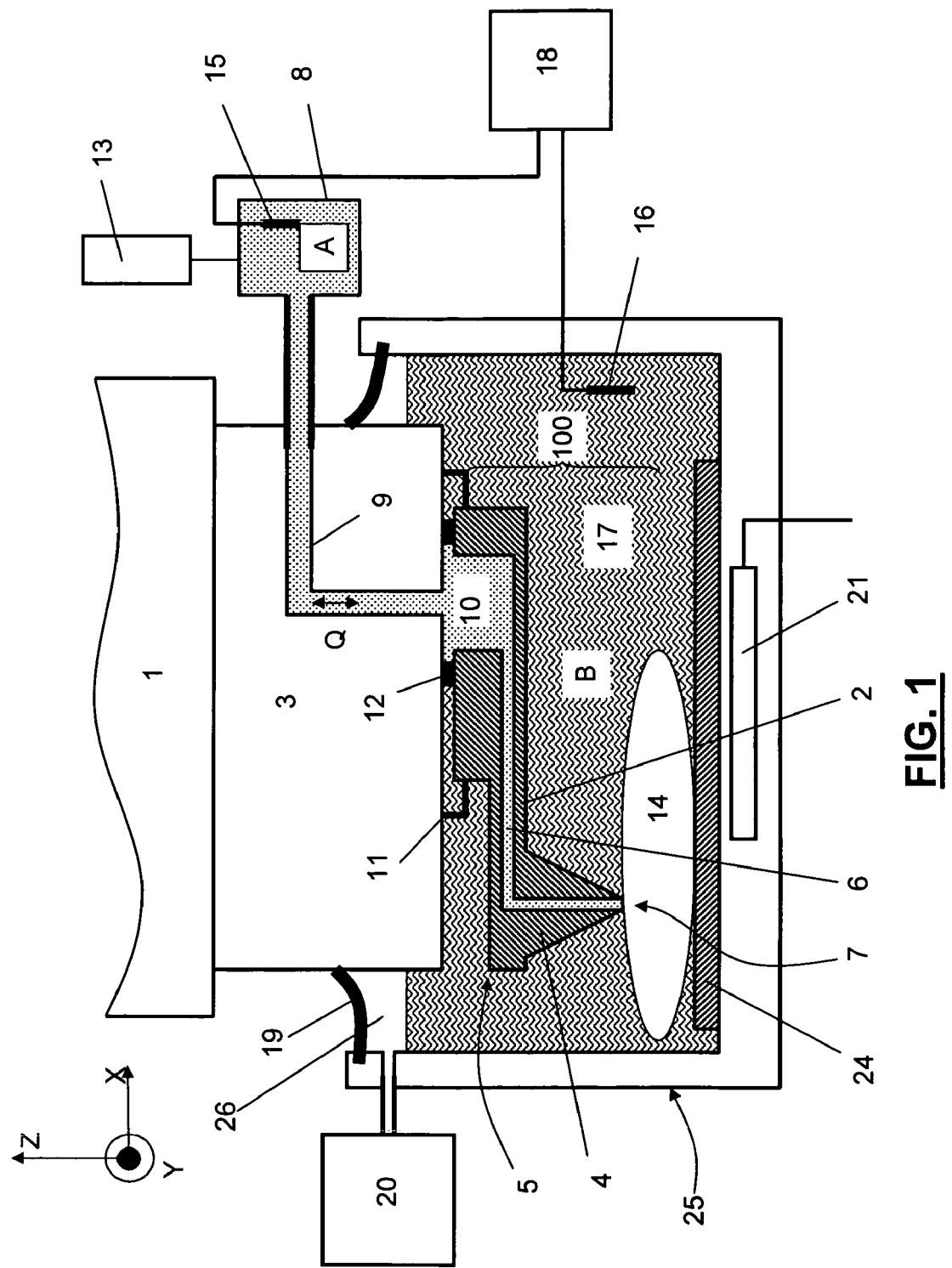
FIG. 1 is a schematic block diagram illustration of a probe arrangement operatively coupled to an AFM head, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate identical or analogous elements but may not be referenced in the description for all figures.

DESCRIPTION OF SOME EMBODIMENTS OF THE INVENTION

In view of the foregoing remarks, it is the object of the present invention to provide an alternative probe arrangement employable, e.g., in the technical field of electrophysiological analysis of cells by means of atomic force microscopy.

The probe arrangement according to some embodiments of the invention may be adapted such to enable the simultaneous employment of at least two of the following operations:
- determining and thus control the normal force of the tip-sample interaction
- operating in various environments (air, liquid)
- performing high resolution topographical imaging of the sample
- choosing the geometry of the cantilever, the geometry of the tip aperture, and the position of the tip aperture,
- selecting a probe with several cantilevers
- selectably releasing and taking up or sucking small amounts of fluids The probe arrangement according to embodiments of the current invention includes a fluid transport channel in the cantilever arm. The fluid reservoir and the duct connecting the fluid transport channel with the fluid reservoir are adapted to be filled with a fluid solution enabling ion transport for electrophysiological analysis and electrochemical tests. In order to enable such electrophysiological analysis and/or to enable electrochemical tests a first electrode is at least placed in the fluid reservoir and/or in the duct and/or in the fluid transport channel.

The presence of means for electrophysiological analysis and/or electrochemical tests greatly increases the number of operating modes at which the probe arrangement is operable in association with atomic force microscopy. For example, the probe arrangement according to embodiments of the invention can be employed in accordance to at least one of the following modes: contact mode, dynamic mode (tapping mode) and force spectroscopy.

In addition, different feedback control modes may be employable enabling the control the interaction between a sample and a probe tip according to at least one of the following control modes: force control using the cantilever deflection detection, "hydraulic" feedback regulating the height of the tip so that the flux of outcoming solution is substantially constant like in SICM. In some embodiments of the invention, a piezoresistive or piezoelectric readout of the cantilever deflection may also be employed.

The proposed solution according to the current invention is also readily adaptable such to be operable in several environments like, for example, fluid environments of biological buffers. Therefore, embodiments of the present invention allow to selectably dispense a first fluid onto and/or into a sample of a biological material that is immerged in a second fluid.

By further providing alternatives in the choice of the geometry or the number of the cantilevers, the geometry of the probe tip aperture, and the position of the probe tip aperture, versatility in terms of application of the probe arrangement may also be enhanced.

In some embodiments of the invention, probe tips may have several alternative geometries, which may be fabricated, for example, by microfabrication of silicon based materials, by soft lithography for polymer based materials or by any other fabrication method, e.g., known in the art. The geometries may be adapted to respective biological application. For example, a first geometry may be employed for the handling of samples, and a second geometry may be employable for the imaging of samples. Correspondingly, the different probe tip ends can have geometries that are for example adapted in accordance to the following techniques being applied: local patch clamp; patch clamp in combination with high resolution imaging; and a tip for intracellular injection.

In some embodiments of the invention, the probe arrangement may include a plurality of cantilever arms, each or at least a number of these cantilever arms having a fluid transport channel, while the probe arrangement can have a plurality of fluid reservoirs, each of these fluid reservoirs being connected via a separate duct to the respective fluid transport channel of the plurality of cantilever arms.

In embodiments of the invention, the probe arrangement can also be such that the cantilever arm of the probe has a plurality of probe tips at the probing end and a fluid transport channel for each or at least a number of the probe tips, while the probe arrangement can have a plurality of fluid reservoirs, each of these fluid reservoirs being connected via a separate duct to the respective fluid transport channels of the cantilever arm.

In some embodiments of the invention, at least one of the fluid reservoirs may be equipped with means enabling pressure and/or flow control for fluid flowing into or out of the fluid channels, i.e., said means enable the probe arrangement to selectably eject and suck in fluid via the fluid transport channel. Thusly configured, fluids can be released close to a cell membrane or injected into a cell either during or before electrophysiological measurements. The suction pressure for patch clamp is therefore controllable such that the respective probe may be sealed on the cell membrane. It should be noted that the term "sealed" also encompasses the term "substantially sealed". Alternatively, the probe arrangement according to embodiments of the invention enables that samples can be selectably withdrawable from proximity of the cell membrane after performing electrical stimulation and electrophysiological measurements on the cell.

A probe arrangement according to the present invention may be used to implement a method for the automatic approach and scanning of cell surfaces and the acquisition of real time topographical images of the cell and features of its membrane. Such a method may include, for example, the following steps: selectably bringing the probe in contact with either the cell or the cell membrane, and into the vicinity of the cell membrane; and releasing or withdrawing through at least one fluid transport channel of the probe a fluid to or from the cell or to or from the vicinity of the cell. The method may further include, e.g., at least one of the following steps: traversing with the probe tip the cell membrane to the interior of the cell; selectably releasing a fluid to the interior of the cell and withdrawing a fluid from the interior of the cell; selectably applying electrophysiological measurements before and during and after bringing the probe into contact with the cell membrane or into the vicinity of the cell membrane; and selectably applying electrical stimulation before and during and after bringing the probe into contact with the cell membrane or into the vicinity of the cell membrane.

It should be noted that the above list of steps should not to be construed as limiting.

Altogether the invention opens up a wide range of possible applications. A none exhaustive list of examples of such applications is given below:

Applications (Without Inserted Electrode)
Onto a substrate in air:
  I. Local release (spotting) of droplets of a solution containing specific molecules or particles for adsorption of these molecules or particles on the substrate after evaporation of the solvent.
  II. Local release of droplets of a solution containing active agents to locally modify the substrate in correspondence of the aperture of the tip.
  III. Release and suction of droplets that captures molecules or nanoparticles adsorbed at the sample surface. The droplets may then be released and analyzed in a mass spectrometer.
Onto a substrate in fluid (solid substrate or soft biological substrate such as a cell):
  IV. Local release (spotting) of one at least one of the following: droplets of a solution containing specific molecules, particles for adsorption of these molecules, and particles on the substrate in fluid environment. Said local releasing eventually prevents or at least substantially diminishes the risk of denaturation of the molecules and/or particles.
  V. Local release of droplets of a solution containing active agents to locally modify the substrate in correspondence of the aperture of the tip.
Into a cell and/or lipid vesicle adsorbed on a substrate in fluid:
  VI. Upon approaching the cell membrane, molecules to which the cell membrane is permeable can be locally released and pass through the cell membrane into the intracellular fluid.
  VII. After the approach with the cell membrane, the tip can be forced in a controlled way to penetrate into the cell to local release (injection) of a solution eventually containing active agents.
From a cell or lipid vesicle adsorbed on a substrate in fluid:
  VIII. Upon approaching the cell membrane, the tip can locally sample (extract) extracellular fluid containing ions or proteins expressed by the cell.
  IX. Upon approaching the cell membrane, the tip can be forced in a controlled way to penetrate into the cell to local sampling (extraction) of the intracellular fluid.
Applications (With Inserted Electrode)
On a conductive substrate in fluid:
  X. Local electroplating of the substrate in correspondence of the aperture of the tip from a solution containing specific metallic ions.
  XI. Local electrochemically driven corrosion of the substrate in correspondence of the aperture of the tip.
On a cell or lipid vesicle adsorbed on a substrate in fluid:
  XII. After approaching the tip onto a cell membrane, electrophysiological tests can be carried out.
From a cell adsorbed on a substrate in fluid:
  XIII. After having electrically stimulated the cell, the tip can be forced in a controlled way to penetrate into the cell to local sampling (extraction) of the intracellular fluid.
Onto a lipid vesicle adsorbed on substrate in fluid:
  XIV. If lipid vesicles functionalized with membrane proteins are adsorbed onto a substrate, the tip can be approached onto one of them to measure the electrical activity of the membrane proteins.
Onto a lipid bilayer deposited onto a porous substrate in fluid:
  XV. If a lipid bilayer functionalized with membrane proteins is deposited on a porous substrate, the tip can be approached onto them to measure the electrical activity of the membrane proteins.

Referring to FIG. 1, a probe arrangement 100 includes a cantilever arm 2 connected to a probe holder 3. Probe holder 3 may be configured, e.g., as known in the art, and may be connected to an AFM head 1, e.g., by conventional mechanical coupling means. A probe of a probe arrangement 100 has a probe tip 4 at a probing end 5 of cantilever arm 2. Cantilever arm 2 includes a fluid transport channel 6 that operatively connects a probe tip aperture 7 with a fluid reservoir 8 via a duct 9. Fluid transport channel 6, duct 9 and fluid reservoir 8 are adapted to be filled with a fluid solution 10 enabling ion transport for electrophysiological analysis.

It should be noted that for the sake of clarity several components known to people skilled in the art have been omitted in FIG. 1, such as the components for force feedback and movement control system for engaging and driving the different AFM modes. For the same reason, various additional parts required for the proper connection of the probe on the probe holder 3, such as clamps 11 or an O-ring 12, are only shown schematically.

Probe holder 3 may be made of any suitable material such as an optically transparent polymer block serving as an interfacing component. The probe itself may be microfabricated and may have at least one cantilever arms 2. Cantilever arm 2 may embed one or more fluid channels 6. Accordingly, the polymer block may be equipped with one or more respective ducts 9.

The dimensions of fluid transport channel 6 or of cantilever arm 2 can be freely chosen, since the probes are microfabricated in cleanroom facilities. Thus, the cantilever spring constant or the cantilever resonance frequency is adaptable for a specific application.

Fluid reservoir 8 is equipped with means 13, e.g. as known in the art enabling pressure and flow control. Such means 13 may be embodied, for example, by a valve and/or pump (not shown) that are operatively connected to a processor (not shown). Consequently, means 13 enable the probe arrangement to eject or suck in fluid from a cell 14 or a cell membrane or some other specimen subjected to electrophysiological analysis. Accordingly, the means 13 for pressure and flow control work both ways as schematically indicated by bi-directional arrow Q. If a plurality of fluid transport channels are provided, a respective plurality of fluid reservoirs may be provided.

For electrophysiological analysis a first electrode is selectably positionable in at least either one of the following: fluid reservoir 8, duct 9 and fluid transport channel 6. It may of course be sufficient that electrical contact with fluid solution 10 in the fluid transport channel 6 is established. A second electrode 16 may be selectably placed into a (e.g. biological) buffer fluid 17 and used as bath electrode or to contact cell 14 or cell membrane. First electrode 15 and second electrode 16 are electrically connected to a control unit 18, which is used for controlling and monitoring the electrophysiological tests and/or patch clamping. Control unit 18 may have interconnections with the systems and components to enable force feedback and movement control.

In operation, the force applied to the probe tip 4, may be measured with a force control unit (not shown), e.g. optically and/ by piezo effect and/or by other means, e.g., known in the art. An automatic mode for example may allow probe tip 4 to approach the sample (e.g. the cell 14) without visual control of the z-axis movement. The feedback loop for the distance approach of probe tip 4 towards the sample can selectably employ e.g. the force signal resulting from the bending of cantilever arm 2 and the electrochemical current probed by the first electrode 15 located in the fluid reservoir 8 or in fluid transport channel 6. These two signals (force and current) can be acquired and used at the same time. In the present example the specimen (e.g., cell 14) to be investigated is positioned in a fluid chamber 25, thereby enabling employing the probe arrangement in a fluid environment. Fluid chamber 25 may contain a buffer fluid 17. Fluid chamber 25 may include a fluid cell sealing 19 to avoid the evaporation of buffer fluid 17. A controller 20 may be operatively connected with sealing 19 to control their position, thus enabling regulating the flow of gas 26 being confined between buffer fluid 17 and sealing 19. Accordingly, controller 20 enables control of the amount of gas 26 being in contact with buffer fluid 17.

Fluid chamber 25 may further be operatively coupled with a heat controller 21 for controlling the temperature of buffer fluid 17.

The probe arrangement according to embodiments of the invention can be employed in both gaseous and liquid environments, since, except for the probe tip aperture 7, microfluid channel 6 may be isolated from the environment, i.e., fluid 10 and fluid 17 may be physically separated.

According to some embodiments, a substrate 24 is placeable within fluid chamber 25. A plurality of biological substances such as, for example, cells, may be placed onto substrate 24. In some embodiments, said cells may constitute an aggregate of cells, i.e., biological tissue. In any event, substrate 24 may be placed on a table (not shown) that is operatively connected with a motion control unit (not shown), which may be implemented, for example, by a drive and a personal computer. The motion control unit may be programmable such that the table may be automatically moveable according to programmed instructions. Thusly configured, the substances placed on substrate 24 are positionable below tip 7 in accordance to a predetermined order, and the analysis of a plurality of substances can be automated.

It should be noted that the probe arrangement may have various configurations. A probe arrangement may for example include a plurality of cantilever arms and/or a plurality of fluid channels. Some of these alternative designs are schematically illustrated in FIG. 2, FIG. 3, FIG. 4A, FIG. 4B and FIG. 5.

Figure 2:
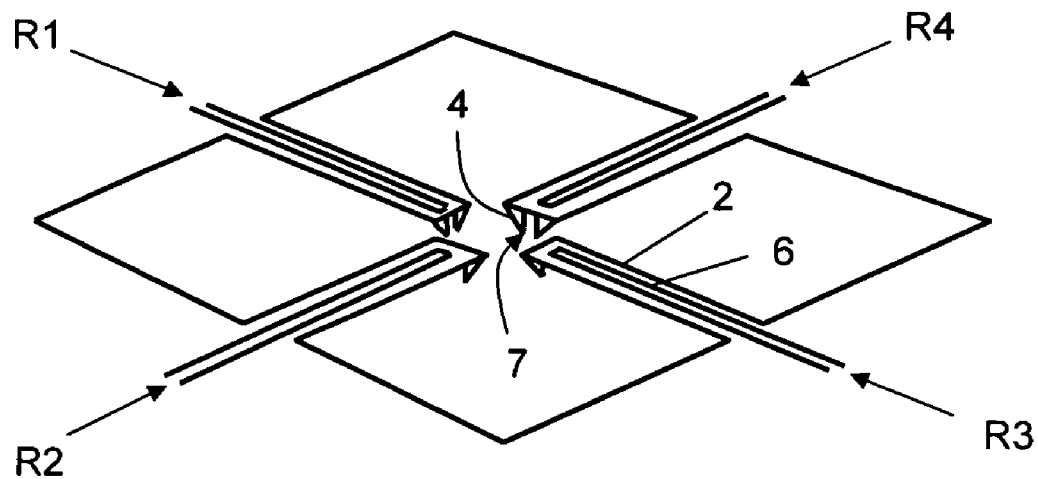
FIG. 2 is a schematic isometric illustration of an array of four cantilever arms that include independent fluid transport channels.

Reference is now made to FIG. 2. An array of four cantilever arms 2 with independent fluid channels 6 (microchannels) is schematically illustrated. Each fluid channel 6 may be connected to an independent fluid reservoir, the latter indicated as R1, R2, R3 and R4. Each cantilever arm 2 may have a probe tip 4 having a probe tip aperture 7. Such an arrangement allows independent force measurement on the same probe, which may be a biological cell.

Figure 3:
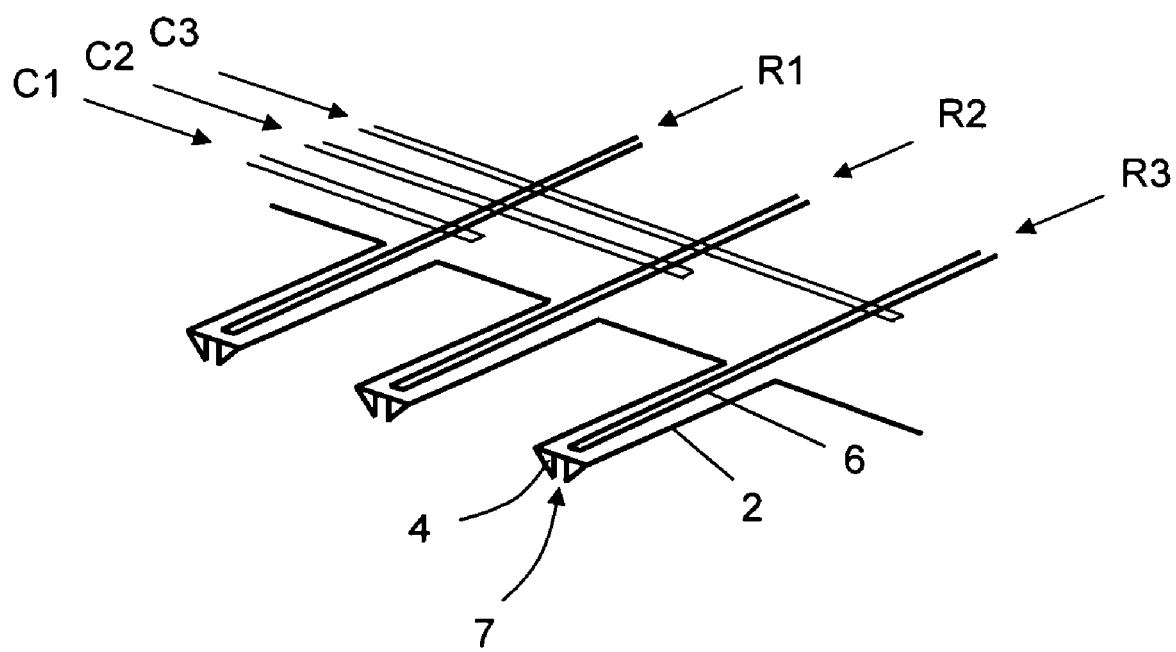
FIG. 3 is a schematic isometric illustration of a one-dimensional array of three cantilever arms that include independent fluid channels according to some embodiments of the invention.

Referring now to FIG. 3, each fluid channel 6 may be connected to an independent fluid reservoir, the latter indicated as R1, R2, and R3. Each cantilever arm 2 may have a probe tip 4 having a probe tip aperture 7. Additionally, each fluid channel 6 may be controlled by a control channel, indicated as C1, C2, and C3. Control channels such as channels C1, C2 and C3 can be employed to selectably open and close the respective fluid channel 6. Control channels C1, C2 and C3 can also be employed as micropumps for drug delivery or suction of the material at the probe tip ends.

Figure 4A:
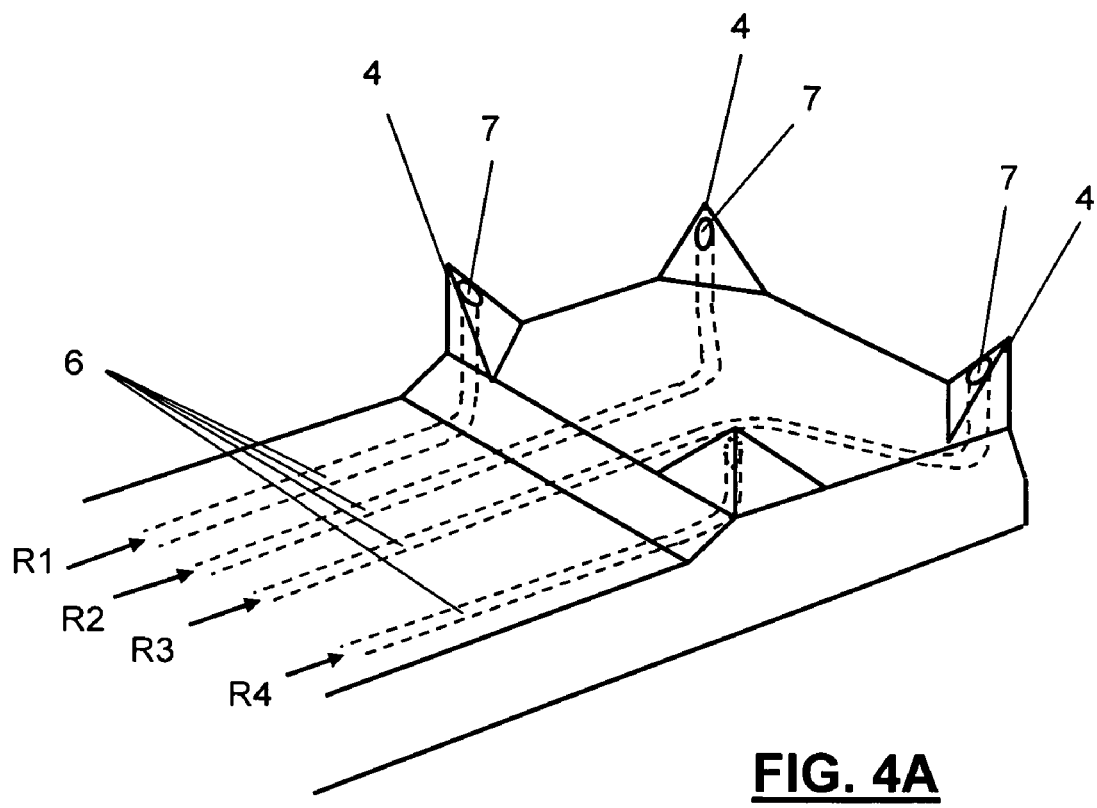
FIG. 4A is a schematic isometric illustration of a cantilever probe having four probe tips and an independent fluid transport channel for each probe tip according to an embodiment of the invention.

Referring now to FIG. 4A, each probe tip 4 may have a probe tip aperture 7. Fluid channels 6 connect the probe tip apertures 7 with corresponding fluid reservoirs R1, R2, R3 and R4. Such an arrangement enables the study of the same cell with different drug deliveries and/or patch clamp techniques with the little pitch (several micrometers) between the tips.

Figure 4B:
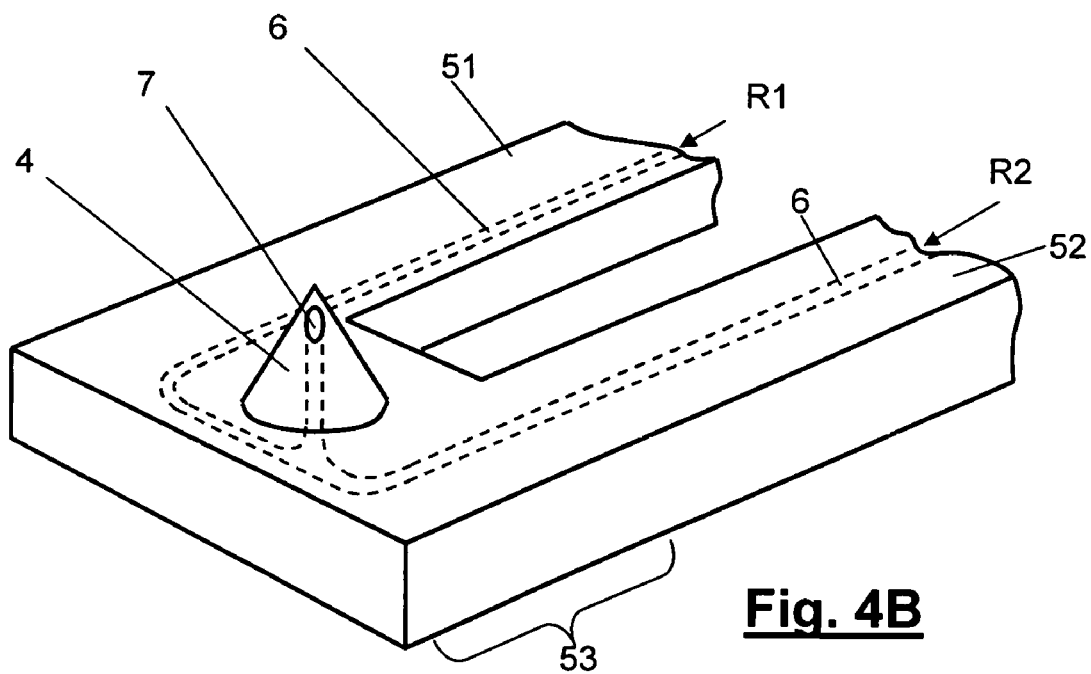
FIG. 4B is a schematic isometric illustration of a U-shaped cantilever probe having one probe tip, according to an alternative embodiment of the invention.

Reference is now made to FIG. 4B. In some embodiments of the invention, a cantilever probe may be U-shaped. Correspondingly, said cantilever probe includes two arms 51 and 52 that are connected to the same base member 53. Arms 51 and 52 may both include fluid channels 6. Each channel 6 may be connected to respective fluid reservoirs R1 and R2, and terminate at base 53 in a common tip aperture 7.

Figure 5A:
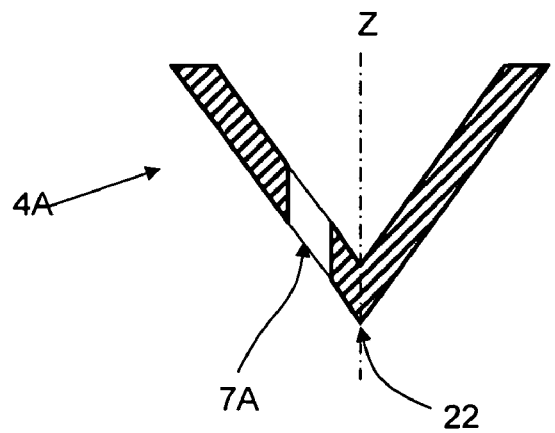
FIG. 5A is a longitudinal section view illustration of a probe tip according to an embodiment of the invention.
Figure 5B:
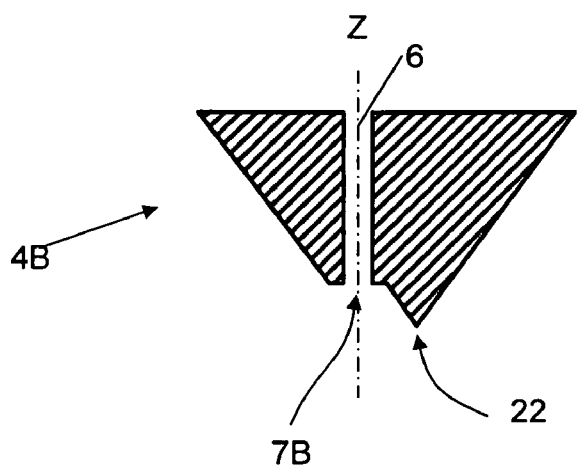
FIG. 5B is a longitudinal section view illustration of a probe tip according to another embodiment of the invention.
Figure 5C:
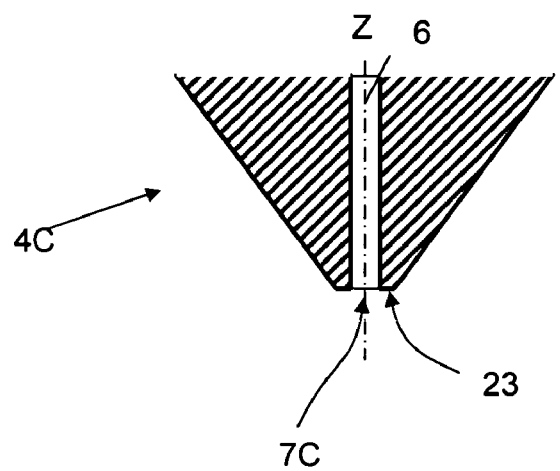
FIG. 5C is a longitudinal section view illustration of a probe tip according to yet another embodiment of the invention.

Referring now to FIG. 5A, FIG. 5B and FIG. 5C, probe tips may have various shapes, optionally with respect to different applications. As is for example schematically illustrated in FIG. 5A, a probe tip 4A have a tapered shape (e.g. substantially conical) terminating in a sharp tip 22. Probe tip 4A may include a probe tip aperture 7A that is arranged off-axis to axis Z at the side of the tapered surface. This type of configuration enables high resolution imaging and local measurement, dispensing and sampling of probes. However, the configuration schematically illustrated in FIG. 5A may not be suitable for patch clamping.

Referring now to FIG. 5B, a probe tip 4B may have a tapered (e.g. generally conical) shape and probe tip aperture 7B may be arranged slightly off-axis on a flattened plateau surface slightly below a sharp tip 22. This type of configuration can be employed for high resolution imaging and may also be employed for patch-clamping.

Referring now to FIG. 5C, a probe tip 4C may have a tapered (e.g. generally conical) shape and a flattened tip 23. A probe tip aperture 7C may be centered and substantially aligned with axis Z. This type of geometry may be suitable for patch-clamping, but may yield only low resolution imaging.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions.

It is to be understood that the phraseology and terminology employed herein is not to be construed as limiting and are for descriptive purpose only.

It is to be understood that the terms "including", "comprising" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

The term "method" refers to manners, means, techniques and procedures for accomplishing a given task including, but not limited to, those manners, means, techniques and procedures either known to, or readily developed from known manners, means, techniques and procedures by practitioners of the art to which the invention belongs.

While the invention has been described with respect to a limited number of embodiments, these should not be construed as limitations on the scope of the invention, but rather as exemplifications of some of the embodiments. Those skilled in the art will envision other possible variations, modifications, and programs that are also within the scope of the invention. Accordingly, the scope of the invention should not be limited by what has thus far been described, but by the appended claims and their legal equivalents.

REFERENCE NUMERALS

1 AFM head
2 Cantilever arm
3 Probe holder
4 Probe tip
5 Probing end
6 Fluid channel
7 Probe tip aperture
8 Fluid reservoir
9 Duct
10 Fluid solution
11 Clamps
12 O-ring
13 Means for pressure and flow control
14 biological material (e.g. a cell, a vesicle, a cell membrane, an artificial lipid bilayer)
15 first electrode
16 second electrode
17 buffer fluid
18 control unit
19 sealing
20 controller for environmental gas
21 heat controller
22 sharp tip
23 flattened tip
24 substrate
25 fluid chamber
26 gas
R1,R2,R3,R4 Reservoirs
C1,C2,C3 Control channels

The invention claimed is:

1. A probe arrangement with a probe for analysis of material for use with atomic force microscopy (AFM), wherein said probe arrangement comprises:
   a cantilever arm connected to a probe holder, wherein said cantilever arm has a thickness in the Y-direction which is greater than the thickness in the Z-direction;
   a sharp, microfabricated probe tip at a probing end of said cantilever arm;
   a fluid channel in said cantilever arm connecting a probe tip aperture with a fluid reservoir via a duct running through said probe holder,
   wherein said fluid channel, said duct and said fluid reservoir are adapted to be filled with a fluid solution enabling ion transport for electrophysiological analysis,
   wherein said fluid reservoir is equipped with a pressure controller and a flow controller in order to enable controlled delivery or suction via said probe tip aperture; and
   wherein a first electrode is suspended in at least one of the following locations: said fluid reservoir; in the duct; and in said fluid channel.

2. The probe arrangement according to claim 1, wherein said probe arrangement comprises:
   a plurality of cantilever arms, at least one of said cantilever arms comprising a fluid transport channel, and a plurality of fluid reservoirs, each of said fluid reservoirs being connected via said duct to said respective fluid channel of said plurality of cantilever arms.

3. The probe arrangement according to claim 1, wherein said at least one cantilever arm of said probe arrangement comprises at least one of a probe tips, and said probe arrangement comprising a plurality of fluid reservoirs, each of said fluid reservoirs being connected via a separate duct to said respective fluid channels of said at least one cantilever arm.

4. The probe arrangement according to claim 1, wherein said probe tip is tapered and terminates in a flattened tip, and wherein a probe tip aperture is located on said flattened tip.

5. The probe arrangement according to claim 4, wherein a sharp tip is located on said flattened tip.

6. The probe arrangement according to claim 1, wherein said probe tip is tapered and terminates in a sharp tip and wherein said probe tip aperture is arranged off-axis at the side of the tapered surface of said probe tip.

7. A fluid chamber for analysis of material comprising said probe arrangement according to claim 1, containing a buffer fluid in which said probe arrangement operates; and a second electrode in said buffer solution.

8. A method for the automatic approach and scanning of cell surfaces and the acquisition of real time topographical images of the cell and features of its membrane by using a force feedback control system for controlling the probe arrangement of claim 1, wherein said method comprises the following steps:
   obtaining a force-feedback whilst performing at least one of the following in accordance to said force-feedback:
      selectably bringing the probe into contact with either one of the following: said cell, said cell membrane, and into the vicinity of the cell membrane;
      selectably performing through at least one fluid channel of said probe either one of the following: releasing and withdrawing a fluid; and
      performing local electrophysiological measurements.

9. The method of claim 8 comprising the step of traversing with said probe tip the cell membrane to the interior of said cell.

10. The method of claim 8 comprising the step of selectably releasing and withdrawing a fluid to or from the interior of said cell.

11. The method according to claim 8 comprising the step of selectably performing electrophysiological measurements before and during and after bringing said probe tip to one of the following positions; into contact with said cell membrane; and in vicinity of said cell membrane.

12. The method according to claim 8 comprising the step of selectably applying electrical stimulation.

13. The method according to claim 8 comprising the step of selectably employing an electrochemical current and voltage signal probed by said first electrode.

14. The method according to claim 8 comprising the step of using the probe in contact on the sample for patch-clamp techniques.

* * * * *